US007012130B1

(12) United States Patent
Carcagno et al.

(10) Patent No.: US 7,012,130 B1
(45) Date of Patent: Mar. 14, 2006

(54) METHODS OF PURIFYING RECOMBINANT HUMAN ERYTHROPOIETIN FROM CELL CULTURE SUPERNATANTS

(75) Inventors: Carlos Miguel Carcagno, Buenos Aires (AR); Marcelo Eduardo Criscuolo, Capital Federal (AR); Carlos Alberto Melo, Buenos Aires (AR); Juan A. Vidal, Buenos Aires (AR)

(73) Assignee: Sterrenbeld Biotechnologie North America, Inc., Willmington, DE (US)

( * ) Notice: Subject to any disclaimer, the term of this patent is extended or adjusted under 35 U.S.C. 154(b) by 0 days.

(21) Appl. No.: 09/830,964

(22) PCT Filed: Nov. 8, 1999

(86) PCT No.: PCT/US99/26241

§ 371 (c)(1),
(2), (4) Date: Nov. 5, 2001

(87) PCT Pub. No.: WO00/27869

PCT Pub. Date: May 18, 2000

(30) Foreign Application Priority Data

Nov. 6, 1998 (AR) .............................. P980105610
Feb. 23, 1999 (AR) .............................. P990100680

(51) Int. Cl.
C07K 1/00 (2006.01)
A61K 38/00 (2006.01)
(52) U.S. Cl. ....................................... 530/350; 930/90
(58) Field of Classification Search ................ 424/545, 424/520, 529, 579, 563, 555; 514/2, 12, 514/21; 930/90; 530/350
See application file for complete search history.

(56) References Cited

U.S. PATENT DOCUMENTS

| 4,667,016 A | * | 5/1987 | Lai et al. ..................... 530/397 |
| 4,667,195 A | | 5/1987 | Hewick et al. ............. 530/397 |
| 4,703,008 A | * | 10/1987 | Lin ............................. 435/360 |
| 4,806,524 A | | 2/1989 | Kawaguchi et al. ........... 514/8 |
| 5,010,002 A | | 4/1991 | Levinson et al. .......... 435/69.2 |
| 5,547,933 A | | 8/1996 | Lin ............................... 514/8 |
| 5,618,698 A | | 4/1997 | Lin ........................... 435/69.4 |
| 5,688,679 A | | 11/1997 | Powell ..................... 435/240.2 |
| 5,756,349 A | | 5/1998 | Lin ............................ 435/325 |
| 5,783,559 A | | 7/1998 | Florin-Robertsson et al. . 514/12 |

FOREIGN PATENT DOCUMENTS

| WO | WO 86/03520 | | 6/1986 |
| WO | WO 92/06116 | * | 4/1992 |
| WO | WO 98/00530 | | 1/1998 |
| WO | WO 00/27419 | | 5/2000 |
| WO | WO 00/27869 | | 5/2000 |
| WO | WO 00/27997 | | 5/2000 |
| WO | WO 00/28066 | | 5/2000 |

OTHER PUBLICATIONS

Miyake et al. Purification of Human Erythropoietin; Journal of Biological Chemistry, vol. 252, No. 15 (1977), pp. 5558-5564.*
Wojchowksi et al. Site-Specific Antibodies to Human Erythropoietin: Immunoaffinity Purifaction of Urinary and Recombinant Hormone; Biochimica et Biophysica Act-Protein Structure and Molecular Enzymology (1987), 913/2 pp. 170-178.*
Andersen, D.C. and Goochee, C.F., "The effect of cell-culture conditions on the oligosaccharide structures of secreted glycoprotein," *Curr. Op. Biotech.* 5:546-549, Current Biology Ltd. (1994).
Bondurant, M.C. and Koury, M.J., "Anemia Induces Accumulation of Erythropoietin mRNA in the Kidney and Liver," *Mol. Cell. Biol.* 6:2731-3, American Society for Microbiology (1986).
Borsook, H., et al., "Polycythemic Response in Normal Adult Rats to a Nonprotein Plasma Extract from Anemic Rabbits," *Blood* 9:734-742, Grune and Stratton, Inc. (1954).
Bowie, J.U., et al., "Deciphering the Message in Protein Sequences: Tolerance to Amino Acid Substitutions," *Science* 247:1306-1310, American Association for the Advancement of Science (1990).
Brown, P.R. and Krstulovic, A.M., "Practical Aspects of Reverse-Phase Liquid Chromatography Applied to Biochemical and Biomedical Research," *Anal. Biochem.* 99:1-21, Academic Press, Inc. (1979).
Burg, J., et al., "Human erythropoietin recombinant production by fermentation and protein purification using a series of chromatographic steps," *Chem. Abstracts* 126:315 Abstract No. 57095j, American Chemical Society (1997).
Busuttil, R.W., et al., "The Cytological Localization of Erythropietin in the Human Kidney Using the Fluorescent Antibody Technique," *Proc. Soc. Exp. Biol. Med.* 137:327-330, Academic Press, Inc. (1971).
Busuttil, R.W., et al., "Localization of Erythropoietin in the Glomerulus of the Hypoxic Dog Kidney Using a Fluorescent Antibody Technique," *Acta Haemat.* 47:238-242, S. Karger (1972).

(Continued)

*Primary Examiner*—Christopher R. Tate
(74) *Attorney, Agent, or Firm*—Sterne Kessler Goldstein & Fox P.L.L.C.

(57) ABSTRACT

The present invention relates, in general, to a method of purifying recombinant human erythropoietin (EPO). The present invention also relates to a substantially pure EPO. The method comprises a differential precipitation, an hydrophobic interaction chromatography, various concentration and diafiltration steps, tandem anionic and cationic exchange chromatographies and molecular exclusion chromatography for the obtaining of pure EPO. The method does not comprise high performance liquid chromatography steps. The invention also comprises the EPO obtained according to the claimed procedure.

20 Claims, 3 Drawing Sheets

OTHER PUBLICATIONS

Carnot, M.P. and Deflandre, C., "Sur l'activité hémopīétique 'du sérum au cours de la regénération du sang," *C.R. Acad. Sci. 143*:384-386, (1906).

Carnot, M.P. and Deflandre, C., "Sur l'activité hémopīétique des différents organes au cours de la regénération du sang," *C.R. Acad. Sci. 143*:432-435 (1906).

Carnot, M.P., "Sur le Mécanisme de L'hyperglobulie Provoquée par le Sérum D'animaux en Rénovation Sanguine," *C.R.H. Sean. Mem. Soc. Biol. 111*:344-346, Libraires de L'Académie de Médecine (1906).

Carnot, M.P., "Sur L'activité Cytopoiétique du Sang et des Organes Régénérés au Cours des Régénérations Viscérales," *C.R.H. Sean. Mem. Soc. Biol. 111*:463-465, Libraires de L'Académie de Médecine (1906).

Caro, J. and Erslev, A.J., "Biologic and immunologic erythropoietin in extracts from hypoxic whole rat kidneys and in their glomerular and tubular fractions," *J. Lab. Clin. Med 103*:922-931, C.V. Mosby Company (1984).

Caro, J., et al., "Erythropoietin Production by an Established Kidney Proximal Tubule Cell Line (LLCPK$_1$) ," *Exp. Hematol 12*:357, Springer-Veriag (1984).

Caro, J., et al., "Erythropoietin in liver tissue extracts and in liver perfusates from hypoxic rats," *Am. J. Physiol. 244*: E431-E434, American Physiological Society (1983).

Dinkelaar, R.B., et al., "Metabolic Studies on Erythropoietin (Ep): II. The Role of Liver and Kidney in the Metabolism of Ep," *Exp. Hematol. 9*:796-803, Allen Press, Inc. (1981).

Dornfest, B.S., et al., "Hepatic production of erythropoietin in a phenylhydrazine-induced compensated hemolytic state in the rat," *J. Lab. Clin. Med. 102*:274-285, C.V. Mosby Company (1983).

Dornfest, B.S., et al., "Recovery of an Erythropoietic Inducing Factor from the Regenerating Rat Liver," *Ann. Clin. Lab. Sci. 11*:37-46, Institute for Clinical Science (1981).

Erslev, A., "Humoral Regulation of Red Cell Production," *Blood 8*:349-357, Grune and Stratton, Inc. (1953).

Erslev, A.J., "In Vitro Production of Erythropoietin by Kidneys Perfused With a Serum-free Solution," *Blood 44*: 77-85, Grune and Stratton, Inc. (1974).

Erslev, A.J. and Caro, J., "Physiologic and Molecular Biology of Erythropoietin," *Med. Oncol. Tumor Pharmacother. 3*:159-164, Pergamon Press (1986).

Eschbach, J.W., et al., "Correction of Anemia of End-Stage Renal Disease with Recombinant Human Erythropoietin," *New Eng. J. Med. 316*:73-78, Massachusetts Medical Society (1987).

Fisher, J.W. and Birdwell, B.J., "The Production of an Erythropoietic Factor by the In Situ Perfused Kidney," *Acta. Haemat. 26*:224-232, S. Karger (1961).

Fisher, J.W., et al., "Localization of Erythropoietin in Glomeruli of Sheep Kidney by Fluorescent Antibody Technique," *Nature 205*:611-612, Macmillan Magazines Ltd. (1965).

Fisher, J.W., "Pharmacologic Modulation of Erythropoietin Production, " *Ann. Rev. Pharmacol. Toxicol. 28*:101-122, Annual Reviews, Inc. (1988).

Frenkel, E.P., et al., "Some Observations on the Localization of Erythropoietin," *Ann. N.Y. Acad. Sci. 149*:292-293, New York Academy of Sciences (1968).

Gordon, A.S., et al., "A Plasma Extract with Erythropoietic Activity," *Proc. Soc. Exp. Biol. Med. 86*:255-258, Society for Experimental Biology and Medicine (1954).

Han, F., et al., "Cloning of a human erythropoietin cDNA and its expression in COS-7 cells," *Chem. Abstracts* Abstract No. 511352 (1996).

Hodgson, G. and Tohá, J., "The Erythropoietic Effect of Urine and Plasma of Repeatedly Bled Rabbits," *Blood 9*:299-309, Grune and Stratton, Inc. (1954).

Jacobs, K., et al., "Isolation and characterization of genomic and cDNA clones of human erythropoietin," *Nature 313*: 806-810, Macmillan Magazines Ltd. (1985).

Jacobson, L.O., et al., "Role of the Kidney in Erythropoiesis, " *Nature 179*:633-634, Macmillan Magazines Ltd. (1957).

Jelkmann, W., et al., "Extraction of Erythropoietin from Isolated Renal Glomeruli of Hypoxic Rats," *Exp. Hematol. 11*:581-588, Allen Press, Inc. (1983).

Jixian, D., et al., "Study on a serum-free medium used for production of rHuEPO," *Bull. Acad. Mil. Med. Sci. 21*:244-246, Academy of Military Medical Sciences (1997).

Kazal, L.A. and Erslev, A.J., "Erythropoietin Production in Renal Tumors," *Ann. Clin. Lab. Sci. 5*:98-109, Institute for Clinical Science (1975).

Krane, N.K., "The Role of Erythropoietin in the Anemia of Chronic Renal Failure," *H. Ford Hosp. Med. J. 31*:177-181, Henry Ford Hospital (1983).

Koury, S.T., et al., "Localization of Erythropoietin Synthesizing Cells in Murine Kidneys by In Situ Hybridization," *Blood 71*:524-527, Grune and Stratton, Inc. (1988).

Koury, S.T., et al., "Quantitation of Erythropoietin-Producing Cells in Kidneys of Mice by In Situ Hybridization: Correlation With Hematocrit, Renal Erythropoietin mRNA, and Serum Erythropoietin Concentration," *Blood 74*:645-651, Grune and Stratton, Inc. (1989).

Kuratowska, Z., et al., "Studies on the Production of Erythropoietin by Isolated Perfused Organs," *Blood 18*:527-534, Grune and Stratton, Inc. (1961).

Kurtz, A., et al., "Renal mesangial cell cultures as a model for study of erythropoietin production," *Proc. Natl. Acad. Sci. USA 80*:4008-4011, National Academy of Sciences (1983).

Lacombe, C., et al., "Peritubular Cells Are the Site of Erythropoietin Synthesis in the Murine Hypoxic Kidney," *J. Clin. Invest. 81*:620-623, Rockefeller University Press (1988).

Liu, P., et al., "Hepatic Erythropoietin (Ep) Production Following Double Partial Hepatectomy in the Rat," *J. Surg. Oncol. 15*:121-132, Alan R. Liss, Inc. (1980).

Naughton, B.A., et l., "Reticuloendothelial System (RES) Hyperfunction and Erythropoietin (Ep) Production in the Regenerating Liver," *J. Surg. Oncol. 12*:227-242, Alan R. Liss, Inc. (1979).

Naughton, B.A., et al., "Evidence for a Hepatic-Renal Antagonism in the Production of Hepatic Erythropoietin," *Ann. Clin. Lab. Sci. 13*:432-438, Institute for Clinical Science (1983).

Parsons, T.F., et al., "Rapid and Easy Separation of the Subunits of Bovine and Human Glycoprotein Hormones by Use of High Performance Liquid Chromatography," *Endocrinology 114*: 2223-2227, J.B. Lippincott Co. (1984).

Reisman, K.R., "Studies on the Mechanism of Erythropoietic Stimulation in Parabiotic Rats During Hypoxia," *Blood 5*:372-380, Grune and Stratton, Inc. (1950).

Schuster, J.H., et al., "Physiologic Regulation and Tissue Localization of Renal Erythropoietin Messenger RNA," *Blood 70*:316-318, Grune and Stratton, Inc. (1987).

Sherwood, J.B., et al., "Erythropoietin Production by Human Renal Carcinoma Cells in Culture," *Endocrinology* 99:504-510, J.B. Lippincott Co. (1976).

Takagaki, Y., et al., "Amino Acid Sequence of the Membranous Segment of Rabbit Liver Cytochrome $b_5$," *J. Biol. Chem.* 255:1536-1541, American Society of Biological Chemists, Inc. (1980).

Werbor, M.K., et al., "Preliminary purification of two human blood cell hormones by hydrophobic interaction chromatography," *Chem. Abstracts 100*:77 Abstract No. 203779a, American Chemical Society (1984).

Pending Non-Provisional U.S. Appl. No. 09/830,967, Carcegno et al., filed May 3, 2001.

Pending Non-Provisional U.S. Appl. No. 09/830,968, Carcegno et al., filed May 3, 2001.

International Search Report of International Application No. PCT/US99/26238, Mar. 7, 2000.

International Search Report of International Application No. PCT/US99/26241, Mar. 7, 2000.

International Search Report of International Application No. PCT/US99/26240, Feb. 22, 2000.

International Search Report of International Application No. PCT/US99/26237, Feb. 18, 2000.

\* cited by examiner

Fig. 1. Polyacrylamide gel electrophoresis (SDS-PAGE)
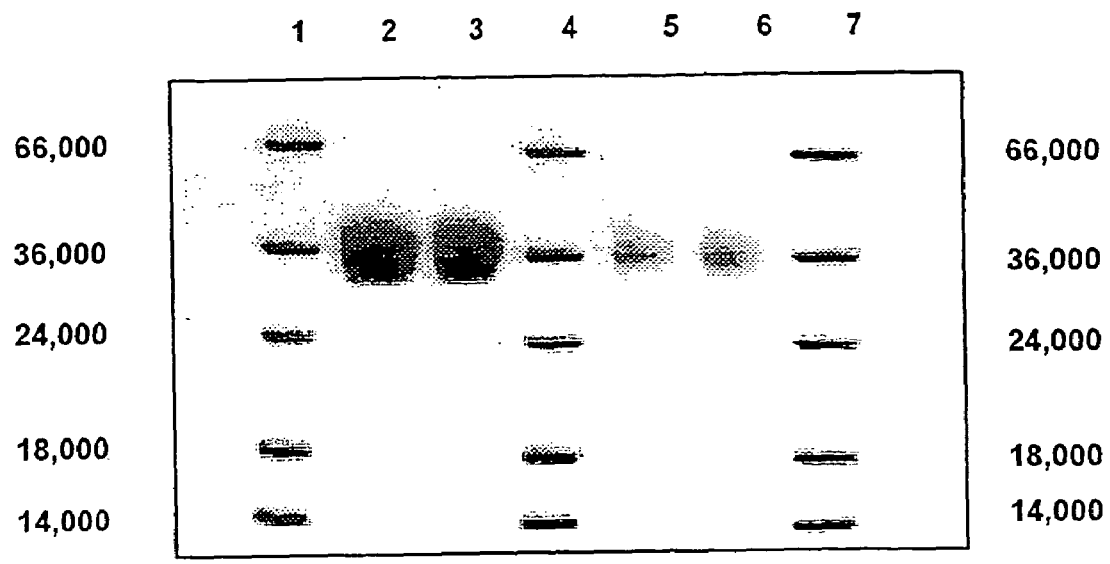
Fig. 2. Western blot analysis
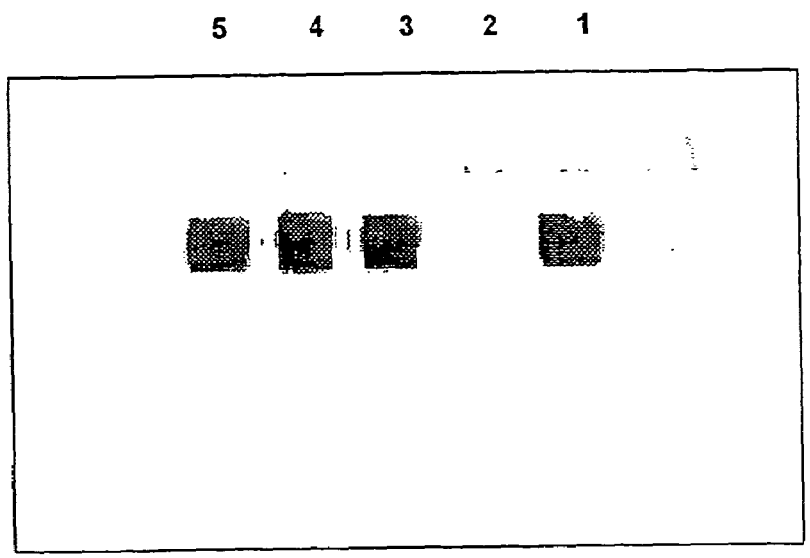

Fig. 3. SDS-PAGE analysis of EPO digestion with glycanases
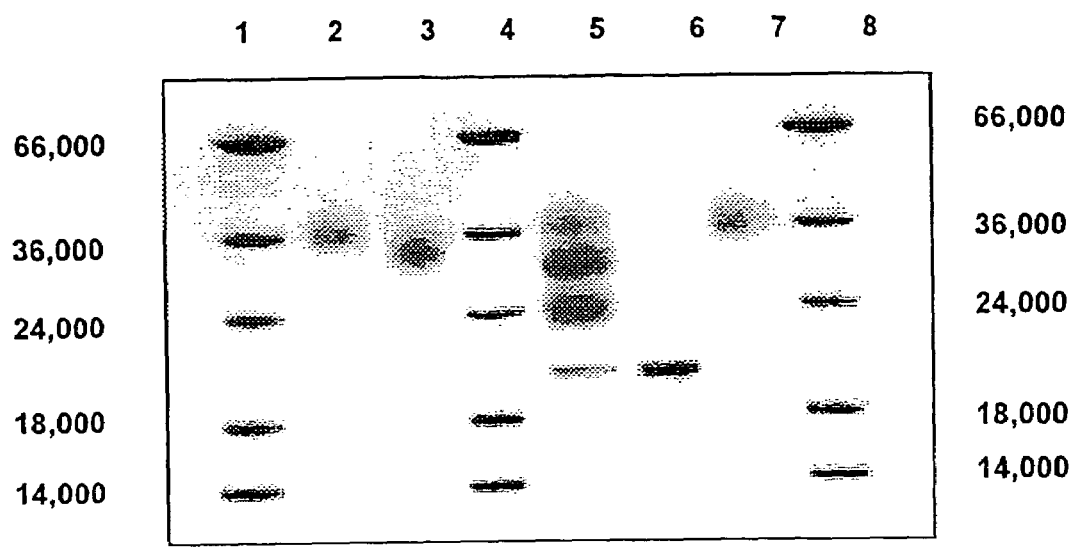
Fig. 4. Determination of isoelectric point (isoelectric focusing)
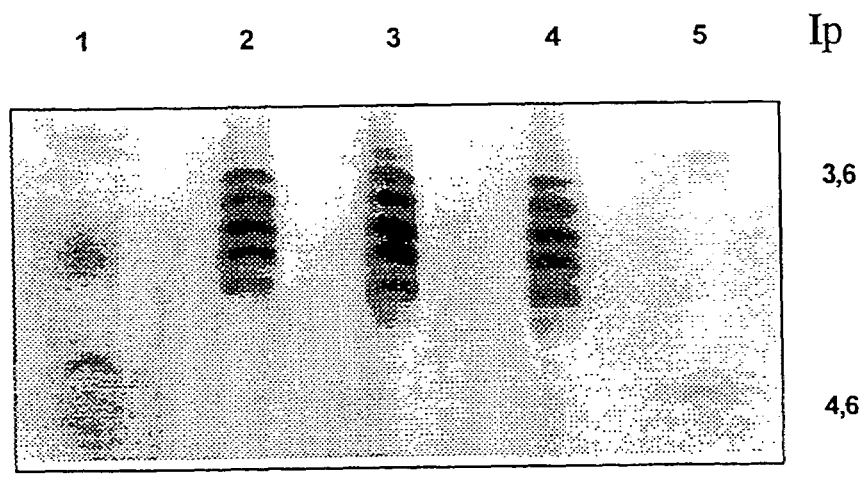

Fig. 5. Reverse phase high performance liquid chromatography
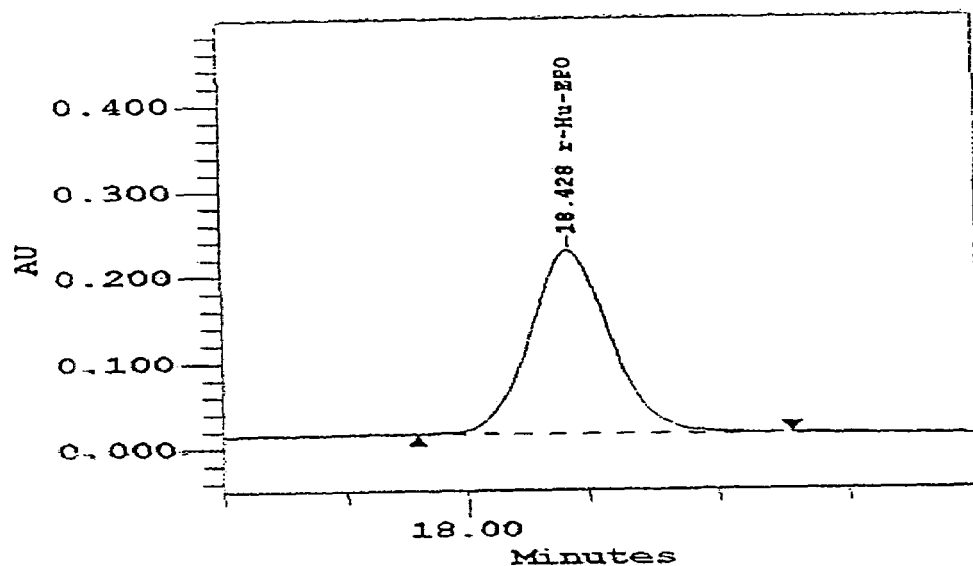
Fig. 6. Molecular exclusion high performance liquid chromatography
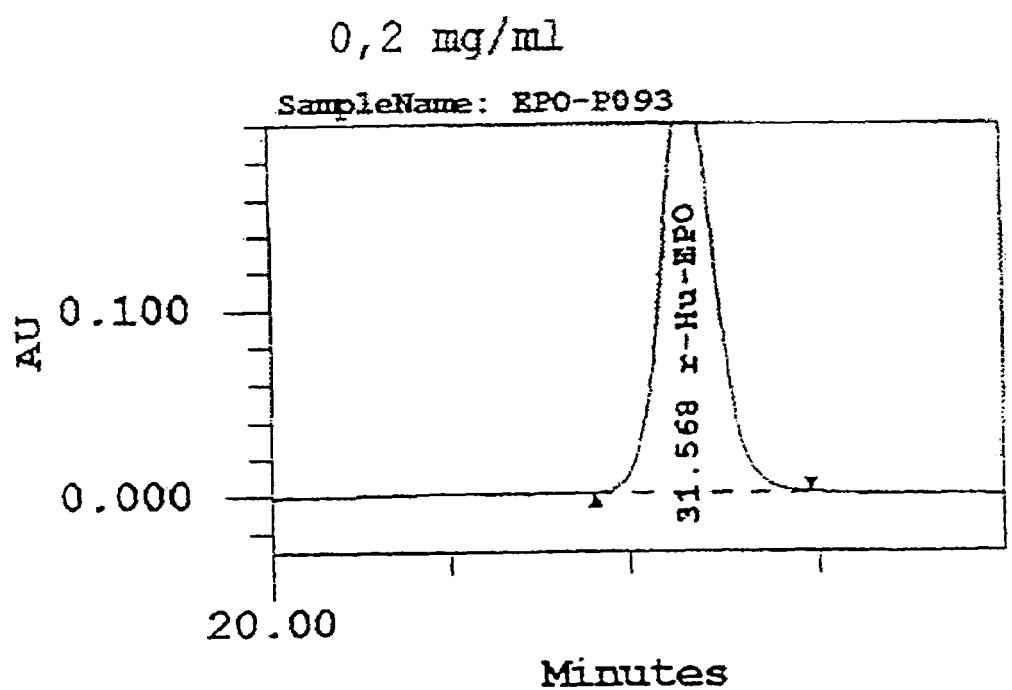

METHODS OF PURIFYING RECOMBINANT HUMAN ERYTHROPOIETIN FROM CELL CULTURE SUPERNATANTS

This application claims benefit under 35 U.S.C. § 371 of International Application No. PCT/US99/26241, filed on 8 Nov. 1999, which was published under PCT Article 21(2) in English and which is fully incorporated herein by reference.

BACKGROUND OF THE INVENTION

1. Field of the Invention

Methods to obtain recombinant human erythropoietin (EPO) characterized by a sequence of tandem separation steps that includes differential precipitation, hydrophobic interaction, anionic exchange, cationic exchange and molecular exclusion liquid chromatographies. The EPO obtained by using the methods thus described.

2. Background Information

EPO is a glycoprotein that stimulates erythroblast differentiation in the bone marrow, thus increasing the circulating blood erythrocyte count. The mean life of erythrocytes in humans is 120 days and therefore, a human being losses 1/120 erythrocytes each day. This loss must be continuously restored to maintain a stable level of red blood cells.

The existence of EPO was first postulated by the turn of the century and was definitely proved by Reissman and Erslev early in the '50s. See Carnot, et al., *C.R. Acad. Sci.* (France), 143, 384–6 (1906); Carnot, et al., *C.R. Acad. Sci.* (France), 143, 432–5 (1906); Carnot, et al., *C.R. Soc. Biol.*, 111, 344–6 (1906); Carnot, *C.R. Soc. Biol.*, 111, 463–5 (1906); Reissman, *Blood*, 1950, 5, 372–80 (1950) and Erslev, *Blood*, 8, 349–57 (1953). Reissman and Erslev's experiments were promptly confirmed by other researchers. See Hodgson, et al., *Blood*, 9, 299–309 (1954); Gordon, et al., *Proc. Soc. Exp. Biol. Med.*, 86, 255–8 (1954) and Borsook, et al., *Blood*, 9, 734–42 (1954).

The identification of the EPO production site in the organism was an issue of debate. Successive experiments led to identify the kidney as the main organ and peritubular interstitial cells as the synthesis site. See Jacobson, et al., *Nature*, 179, 633–4 (1957); Kuratowska, et al., *Blood*, 18, 527–34 (1961); Fisher, *Acta Hematol.*, 26, 224–32 (1961); Fisher, et al., *Nature*, 205, 611–2 (1965); Frenkel et al., *Ann. N.Y. Acad. Sci.*, 149, 1, 292–3 (1968); Busuttil, et al., *Proc. Soc. Exp. Biol. Med.*, 1137, 1, 327–30 (1971); Busuttil, *Acta Haematol.*, (Switzerland), 47, 4, 238–42 (1972); Erslev, *Blood*, 44, 1, 77–85 (1974); Kazal, *Ann. Clin. Lab. Sci.*, 5, 2, 98–109 (1975); Sherwood, et al., *Endocrinology*, 99, 2, 504–10 (1976); Fisher, *Ann. Rev. Pharmacol. Toxicol.*, 28, 101–22 (1988); Jelkrnann, et al., *Exp. Hematol.*, 11, 7, 581–8 (1983); Kurtz, et al., *Proc. Natl. Acad. Sci.* (USA), 80, 13, 4008–11 (1983); Caro, et al., *J. Lab. Clin. Med.*, 103, 6, 922–31 (1984); Caro, et al., *Exp. Hematol.*, 12, 357 (1984); Schuster, et al., *Blood*, 70, 1, 316–8 (1986); Bondurant, et al., *Mol. Cell. Biol.*, 6, 7, 2731–3 (1986); Bondurant, et al., *Mol. Cell. Biol.*, 6, 7, 2731–3 (1986); Schuster, et al., *Blood*, 71, 2, 524–7 (1988); Koury, et al., *Blood*, 71, 2, 524–7 (1988); Lacombe, et al., *J. Clin. Invest.*, 81, 2, 620–3 (1988); Koury, et al., *Blood*, 74, 2, 645–51 (1989).

A smaller proportion, ranging from 10% to 15% of total EPO, is produced by the liver in adults. See Naughton, et al., *J. Surg. Oncol.*, 12, 3, 227–42 (1979); Liu, et al., *J. Surg. Oncol.*, 15, 2, 121–32 (1980); Dornfest, et al., *Ann. Clin. Lab. Sci.*, 11, 1, 37–46 (1981); Dinkelaar, et al., *Exp. Hematol.*, 9, 7, 796–803 (1981); Caro, et al., *Am. J. Physiol.*, 244, 5 (1983); Dornfest, et al., *J. Lab. Clin. Med*, 102, 2, 274–85 (1983); Naughton, et al., *Ann. Clin. Lab. Sci.*, 13, 5, 432–8 (1983); Jacobs, et al., *Nature*, 313, 6005, 806–10 (1985); Erslev, et al., *Med. Oncol. Tumor. Pharmacother.*, 3, 3–4, 159–64 (1986). The EPO produced is directly proportional to the extent of tissular hypoxia and its expression rises by increasing the number of the EPO producing cells.

EPO has shown great efficiency in the treatment of anemia, especially anemia derived from renal failure. See Eschbach, et al., *N. England J. of Med.*, 316, 2, 73–78 (1987); Krane, *Henry Ford Hosp. Med J.*, 31, 3, 177–181 (1983). Its therapeutical usefulness, however, has been limited due to the unavailability of a massive production method. The quantity and quality of the EPO obtained by the extractive systems known were insufficient. Recently, the use of recombinant DNA technology has made it possible to obtain large amounts of proteins. The application of these techniques to eukaryotic cells has allowed a large scale production of EPO. See U.S. Pat. No. 5,688,679 (to Powell), U.S. Pat. No. 5,547,933 (to Lin), U.S. Pat. No. 5,756,349 (to Lin), U.S. Pat. No. 4,703,008 (to Lin) and U.S. Pat. No. 4,677,195 (to Hewick et al.).

Several techniques for the separation of glycoproteins such as EPO are currently available. Ultrafiltration, column electrofocusing, flat-bed electrofocusing, gel filtration, electrophoresis and isotachophoresis and some others chromatographic methods have been utilized for the purification of glycoproteins. The most widely used chromatographic techniques have been ionic exchange chromatography and adsorption chromatography.

The ionic exchange method is a separation technique by which the components of a solution are distinguished according to their different net charges and isolated by elution, either in stages or through the application of a continual gradient, with eluents of different ionic strength or pH. This method employs a gel or resin matrix, either of positive or negative charge, to induce binding or electrostatic adsorption of components with opposite charges. During desorption or elution, sample components are exchanged by ions present in the solution or buffer used to elute, or by a change in pH that alters the net charge of the molecule of interest.

Reverse phase adsorption chromatography involves separating the sample components according to their different polarities. Sample components are adsorbed through a resin composed of a silica matrix covered with an organic polymer by non-covalent bonding. The selective desorption of the components occurs afterwards by the elution with a non-polar solvent containing the eluent.

The separation techniques described above were utilized initially to separate relatively small hydrophobic or hydrophilic molecules. Their application to the purification of larger molecules, such as proteins, and specially complex proteins such as lipoproteins, nucleoproteins and glycoproteins, is more recent. Numerous publications illustrate the state of the art attained so far in protein separation.

See Soferet et al., "Handbook of Process Chromatography" (Academic Press Inc., San Diego, Calif., 1997); Olson, Ed., "Separation Technology" (Interpharm Press, Inc., Buffalo Grove, Ill., 1995); Franks, Ed., "Protein Biotechnology" (Human Press, Totowa, N.J., 1993); Deutscher, Ed., "Guide to Protein Purification, Methods in Enzymology", Vol. 182, (Academic Press Inc. San Diego, Calif., 1991); Seetharam et al., Eds., "Purification and Analysis of Recombinant Proteins" (Marcel Dekker, Inc., New York, N.Y., 1991); Harria et al., Eds., "Protein Purification Applications" (Oxford University Press, Oxford, England, 1990); Brown, et al., *Analytical Biochemistry*, 99, 1–21, 1979; Harrison et al., "VDYAC TM Comprehensive Guide to Reverse Phase Materials for HPLC", pp. 1-12 (The Sep/A/Ra/Tions Groups, Hesperia, Calif., 1984). The use of monoclonal antibodies raised against the protein of interest is another known method of protein recovery.

Several specific methods for recombinant EPO separation have been recently reported. One of these methods consists in protein purification by anionic exchange chromatography with selective protease elimination, followed by reverse phase chromatography and filtration. See U.S. Pat. No. 4,667,016 (to Lai et al.). This technique claims a yield of 16% EPO of unknown specific activity and purity.

Another method proposed for the separation of recombinant EPO consists in the application of reverse phase high pressure liquid chromatography (RP-HPLC) to a solution containing partially purified protein. See U.S. Pat. No. 4,667,195 (to Hewick et al.). This method has been found irreproducible in practice. Morever, the non-polar solvents commonly employed or recommended for protein and polypeptide separation by means of RP-HPLC, include reagents such as acetonitrile, difficult to remove from the protein of interest and potentially toxic for human beings. See Parsons, et al., *Endocrinology*, 114, 6, 2223–7 (1984). It should be noted, however, that ethanol and formic acid aqueous solutions for protein elution have also been used. See Takagaki, et al., *Journal of Biological Chemistry*, 5, 4, 1536–41 (1980).

Even though there is abundant information regarding the production of recombinant human EPO, a purification method yielding EPO adequate for its utilization in human beings has not yet been described. A suitable protein purification method should yield EPO over 99% pure and free of contaminants such as: aggregated material, b) degraded material, c) spurious proteins and d) proteases. A protein purity under 99% or the presence of any of the above mentioned contaminants might be toxic for human beings.

On the other hand, many of the methods proposed for EPO purification are not efficient when applied to industrial scale protein production. The RP-HPLC method employs expensive organic solvents, which increases purification costs. In addition, organic solvents are more difficult to handle and contaminant to the environment. Other purification methods proposed are irreproducible in practice or have a low yield.

SUMMARY OF THE INVENTION

The novel method of the present invention describes, in detail, a system for EPO purification whereby a high recovery of a product of high purity and quality is achieved. This product may be used without further purification to formulate pharmaceutical compounds as injectable products for use in human medicine.

An advantage of the claimed invention is the attainment of EPO protease free without any undesirable molecular variants such as aggregates, degraded material or molecules of unexpected isoelectric point values. The EPO obtained by the claimed invention is over 99% pure and could be utilized to prepare pharmaceutical formulations adequate for administration to human beings without any additional purification step. The EPO obtained by the claimed invention is a micro-heterogeneous protein comprising between five to eight isoforms with isoelectric points ranging between 3.0 and 4.5 and in vivo specific biological activity over 100,000 IU/mg protein measured by a $^{59}$Fe incorporation ex-hypoxic polycythemic mice assay and an EPO total mass spectophotometric assay at 280 nm.

An additional advantage of the claimed invention is its low environmental impact. The method claimed is a clean process that does not employ separation steps based on RP-HPLC technology, thus avoiding the use of organic solvents that may be harmful to the environment.

Yet another advantage of the claimed invention is the non-exposure of EPO to stringent temperature conditions, harmful organic solvents or other solutions that may affect its biological activity or result in a toxic compound unsuitable for human use.

The following detailed description and examples illustrate the separation steps performed in the claimed method.

BRIEF DESCRIPTION OF THE FIGURES

FIG. 1 illustrates polyacrylamide gel (SDS-PAGE) analysis of an EPO sample obtained following the method described after purification. In lanes 1, 4 and 7, molecular weight markers were loaded. In lanes 2, 3, 5 and 6, different amounts of pure EPO obtained according to the claimed procedure were run. The purity of the product obtained and the apparent molecular weight exceeding 34 kDa is coincident with the one reported for urinary human EPO as could be clearly observed.

FIG. 2 illustrates a Western blot analysis of an EPO sample obtained according to the method described. Identity of the EPO produced is assessed, since it is recognized by a monoclonal antibody against human EPO. In lanes 1 and 2, a human EPO standard and molecular weight markers were loaded, respectively. EPO samples obtained according to the claimed method were loaded in lanes 3 to 5.

FIG. 3 shows a SDS-PAGE analysis of a pure EPO sample obtained according to the method described, treated with glycanases. Molecular weight markers were loaded in lanes 1, 4 and 8. Lanes 2 and 7 correspond to untreated EPO. In lane 3, O-glycanase treated EPO was loaded; the presence of an O-glycosilation site is verified. In lane 5, N-glycanase partially digested EPO was loaded. The presence of 3 N-glycosilated molecules with molecular weights as expected for EPO can be verified. Lane 6 was loaded with EPO digested with N-glycanase, and the expected molecular weight for the wholly deglycosilated protein was obtained.

FIG. 4 illustrates a survey of the isoelectric points in pure EPO samples produced according to the method described. EPO samples were run in lanes 2, 3 and 4, isoelectric point markers in lanes 1 and 5. The presence of isoforms corresponding to EPO are verified, showing an isoelectric point range of 3.0 to 4.5.

FIG. 5 shows the purity of an EPO sample produced according to the method herein described using a reverse phase high performance liquid chromatography.

FIG. 6 illustrate the purity of an EPO sample produced according to the method herein described using a molecular exclusion high performance liquid chromatography.

DETAILED DESCRIPTION OF THE INVENTION

The present invention relates to a method of purifying EPO which comprises treating cell culture supernatants comprising EPO by a combination of the following steps: differential precipitation, hydrophobic interaction chromatography, diafiltration, anionic exchange chromatography, cationic exchange chromatography and molecular exclusion chromatography.

Preferred EPO producing recombinant cells comprise a vector which comprises a nucleotide sequence encoding the EPO polypeptide consisting of the amino acid sequence in SEQ ID NO:1, a viral promoter and a viral terminator. Preferred cells contain vectors which confer resistance to both methotrexate and neomycin-derived antibiotics. Preferably, the EPO nucleic acid molecule comprises the nucleic acid molecule described in Lin, "DNA Sequences Encoding Erythropoietin," U.S. Pat. No. 4,703,008. Preferably, the viral promoter is an SV40 early promoter.

A preferred method of obtaining EPO from recombinant cells is culturing in media comprising insulin. Specifically, such culturing comprises separating the supernatant which comprises EPO and insulin from the host cells of the invention, concentrating the supernatant and freezing the concentrated product. Preferably, the culture media comprises between 0.5 mg and 20 mg insulin per liter of culture media.

The invention further relates to a method of purifying EPO which comprises treating cell culture supernatants comprising EPO by the following steps in order: (a) differential precipitation, (b) hydrophobic interaction chromatography, (c) diafiltration, (d) anionic exchange chromatography, (e) cationic exchange chromatography and (f) molecular exclusion chromatography. The present invention relates to a method of purifying EPO which comprises treating cell culture supernatants comprising EPO by a combination of the following steps: differential precipitation, hydrophobic interaction chromatography, 2 diafiltration steps, anionic exchange chromatography, cationic exchange chromatography and molecular exclusion chromatography.

The invention further relates to a method of purifying EPO which comprises treating cell culture supernatants comprising EPO by a following steps in order: (a) differential precipitation, (b) hydrophobic interaction chromatography, (c) diafiltration, (d) anionic exchange chromatography, (e) cationic exchange chromatography, (e') diafiltration and (f) molecular exclusion chromatography.

The differential precipitation step of the above and below-described methods and compositions comprises adding ammonium sulfate to said supernatant, followed by centrifugation.

The hydrophobic interaction chromatography step of the above and below-described methods and compositions comprises using an hydrophobic interaction matrix. Preferably said interaction matrix is Phenyl Sepharose 6 Fast Flow.

The anion exchange step of the above and below-described methods and compositions comprises using an anion exchange matrix. Preferably said anion exchange matrix comprises Q-Sepharose Fast Flow.

The cation exchange step of the above and below-described methods and compositions comprises using a cation exchange matrix. Preferably said cation exchange matrix comprises SP-Sepharose Fast Flow.

The molecular exclusion step of the above and below-described methods and compositions comprises using a molecular exclusion matrix. Preferably said molecular exclusion matrix is Sephacryl S-200 HP.

In another embodiment, the present invention provides a substantially pure EPO. Preferably, said EPO is produced by a combination of the following steps: differential precipitation, hydrophobic interaction chromatography, diafiltration, anionic exchange chromatography, cationic exchange chromatography and molecular exclusion chromatography. More preferably, said EPO has a purity of greater than 99% as determined by SDS-PAGE gel electrophoresis.

A preferred method of using the purified EPO of the present invention comprises lyophilization into a form suitable for injection into humans for treatment of disease. Specifically, the preferred lyophilization procedure comprises placing the EPO into a pharmaceutical composition, loading the first EPO composition into a container, wherein said container is at a temperature equal to or less than −30° C.; incubating said EPO composition at a temperature equal to or less than −30° C. under atmospheric pressure for a time equal to or greater than 4 hours; incubating said composition at a pressure of equal to or less than 30 absolute microns for a time equal to or greater than one hour; and raising the temperature equal to or less than 3° C. per hour until reaching at least 25° C., while keeping pressure values equal to or less than 5 absolute microns.

A preferred pharmaceutical composition for lyophilization comprises EPO, sugar, salts and human albumin. An especially preferred composition for lyophilization comprises EPO, mannitol, NaCl, $NaH_2PO_4$ and $Na_2HPO_4 \cdot 12H_2O$.

The present invention is described in further detail in the following non-limiting examples.

EXAMPLES

Example 1

Recovery 7,920 g of ammonium sulfate were dissolved in 30 liters of sterile concentrated solution obtained from culturing CHO (Chinese Hamster Ovary) cells producing EPO. After addition of ammonium sulfate, the solution was stored at 4° C. for 24 hours. Many contaminant proteins precipitated while the EPO remained in solution. The product was centrifuged at 5,000 RPM for 10 minutes in a Sorvall centrifuge, using a HG4L rotor.

Example 2

Hydrophobic Interaction Chromatography

The material obtained from the previous step is chromatographed using an Hydrophobic Interaction matrix (Phenyl Sepharose 6 Fast Flow low sub-Pharmacia) according to the following parameters:

1. Equipment:
   A. Pre-column:
      1) Diameter: 14 cm
      2) Bed height: 19 cm
      3) Matrix:
         a) Q-Sepharose Big Bead (Pharmacia)
         b) Volume: 3,000 ml
   B. Column:
      1) Diameter: 20 cm
      2) Bed height: 19 cm
      3) Matrix:
         a) Phenyl-Sepharose 6 Fast Flow low sub. (Pharmacia)
         b) Volume: 6,000 ml
2. Solutions and buffers:
   A. Buffer A: 10 mM $NaH_2PO_4$, pH 7.2
   B. Buffer F: 10 mM $NaH_2PO_4$, 1.8 M $(NH_4)_2SO_4$, pH 7.2
   C. Buffer G: 150 mM $NaH_2PO_4$, pH 7.2
   D. 20% isopropyl alcohol
   E. 0.5 N NaOH 3. Material to be chromatographed:
   A. Ammonium sulfate supernatant resulting from previous example.
   B. Sample conditions:
      1) Volume: 30,000 ml
      2) Conductivity: 190–210 mSi/cm
      3) pH: 7.2

To equilibrate and sanitize the pre-column the following solutions or buffers in the quantities hereinafter detailed were sequentially passed through it: 1.0 volume of the column ("vc") (3 l) of $H_2O$; 1.0 vc (3 l) of NaOH 0.5N, 1.0 vc (3 l) of Buffer G and finally 1.5 vc (4.5 l) of Buffer F.

To equilibrate the column the following solutions or buffers in the quantities hereinafter detailed were sequentially passed through it: 1.0 vc (6 l) of $H_2O$; 1.0 vc (6 l) of 20% isopropyl alcohol; 1.0 vc (6 l) of $H_2O$; 1.0 vc (6 l) of 0.5 N NaOH; 1.0 vc (6 l) of $H_2O$; 1.0 vc (6 l) of Buffer G and finally 1.5 cv (9 l) of Buffer F.

Once the pre-column and the column were equilibrated, the column was connected after the pre-column and the material to be chromatographed was loaded. Said loading was performed at 4° C., at a 19 cm/hour flow. Thereafter, the elution was performed at the same flow rate but at room temperature, and the solutions and buffers hereinafter detailed were passed through the columns in the following quantities and order: 2.5 vc (15 l) of Buffer F, (once this buffer has passed through, the pre-column was removed). Once the pre-column was removed, the chromatography was performed on the Phenyl Sepharose column on which a Buffer F-Buffer A gradient was applied starting from a 85:15 ratio of said buffers until 50:50 ratio of said buffers in a total volume of 10 vc (60 l) was reached.

When the gradient was finished, 1.5 vc (9 l) of Buffer F-Buffer A in a 30:70 ratio was passed through the column and finally 1.5 vc (9 l) of $H_2O$. The selected EPO containing fractions were filtered under sterile conditions through a 0.22 μm pore membrane and stored at 4° C.

Example 3

Concentration and Diafiltration

The fractions resulting from the previous example were concentrated and diafiltered according to the conditions described below:

1. Equipment:
   A. Peristaltic pump: Watson Marlow - Cat. N° 302S
   B. Tubing: Masterflex - Cat. N° 06402-18
   C. Concentrator: Prep Scale Millipore CDU F006LC
2. Solutions and buffers:
   A. 10 mM Sodium Dodecyl Sulfate (SDS)
   B. 1 mM Triton X-100
   C. 0.1 N NaOH
   D. $H_2O$
   E. Buffer A: 10 mM $NaH_2PO_4$, pH 7.2
3. Material to be processed:
   A. Selected fractions resulting from the previous example.
   B. Sample conditions:
      1. Volume: 15,000–30,000 ml
      2. Conductivity: 130–170 mSi/cm
      3. pH: 7.2

The equipment was first cleaned, sanitized and equilibrated, and the following sequence of solutions and buffers were flowed through the equipment: 10 l of 10 mM SDS; 40 l of $H_2O$; 10 l of 1 mM Triton X-100, 40 l of $H_2O$; 10 l of 0.1N NaOH; 40 l of $H_2O$ and finally 5 l of Buffer A. The equipment was then ready to be used for concentration and diafiltration against Buffer A on the selected fractions, following the usual methodology.

The final volume of the concentrated product was between 2,000 to 3,000 ml, its conductivity was 1,100–1,550 μmSi/cm and its pH was 7.2.

Example 4

Anionic Exchange Chromatography

The material resulting from the previous example was chromatographed using an anionic exchange matrix, as follows:

1. Equipment:
   A. Column:
      1) Diameter: 14 cm
      2) Bed height: 19 cm
      3) Matrix
         a) Q-Sepharose Fast Flow (Pharmacia)
         b) Volume: 3,000 ml
2. Solutions and buffers:
   A. Buffer A: 10 mM $NaH_2PO_4$, pH 7.2
   B. Buffer G: 150 mM $NaH_2PO_4$, pH 7.2
   C. Buffer N: 50 mM Acetic Acid, 500 mM NaCl, pH 4.0
   D. Buffer S: 50 mM Acetic Acid, pH 4.0
   E. 0.5 N NaOH
3. Material to be chromatographed
   A. Fractions selected from the hydrophobic interaction step, duly concentrated and diafiltered.
   B. Sample conditions:
      1) Volume: 2,000 to 3,000 ml
      2) Conductivity: 1,100–1,550 μSi/cm
      3) pH: 7.2

To equilibrate the column the following solutions or buffers in the quantities hereinafter detailed were sequentially passed through it: 1.0 vc (3 l) of $H_2O$; 1.0 vc (3 l) of 0.5 N NaOH; 1.0 vc (3 l) of Buffer N, 2.0 vc (6 l) of Buffer S; 3.0 vc (9 l) of Buffer G; and finally 2.0 vc (6 l) of Buffer A.

Once the column was equilibrated, the material to be chromatographed was loaded. Said loading was performed at room temperature at 39 cm/hour. Thereafter, the elution was performed at the same flow rate and temperature, and the solutions and buffers hereinafter detailed were passed in the following order: 1.0 vc (3 l) of Buffer A and 4.0 vc (12 l) of Buffer S. Thereafter, a Buffer S-Buffer N step (50:50) in a total volume of 1.5 vc (4.5 l) was performed.

Once the step finished, 1.5 vc (4.5 l) of Buffer N was passed through the column. The selected EPO containing fractions, were filtered under sterile conditions through a 0.22 μm pore membrane and stored at 4° C.

Example 5

Cationic Exchange Chromatography

The material resulting from the previous example was chromatographed using a cationic exchange matrix, as follows:

1. Equipment:
   A. Column:
      1) Diameter: 14 cm
      2) Bed height: 19 cm
      3) Matrix
         a) SP-Sepharose Fast Flow (Pharmacia)
         b) Volume: 3,000 ml
2. Solutions and buffers
   A. Buffer D: 12.5 mM $Na_2HPO_4$, 4 mM Citric acid, pH 6.0
   B. Buffer E: 12.5 mM $Na_2HPO_4$, 4 mM Citric acid, 0.5 M NaCl, pH 6.0
   C. 0.5 N NaOH
3. Material to be chromatographed
   A. Fraction selected from the previous example adjusted to pH 6.0 with NaOH cc and diluted until reaching a conductivity of 4,800 $\mu$Si/cm (conductivity equal to Buffer D-Buffer E in a 93.5:6.5 ratio).
   B. Sample conditions:
      1) Volume: 5,000 ml
      2) Conductivity: 4,800 $\mu$Si/cm (equal to Buffer D-Buffer E in a 93.5:6.5 ratio).
      3) pH: 6.0

To equilibrate the column, the following solutions or buffers in the quantities hereinafter detailed were sequentially passed through it: 1.0 vc (3 l) of $H_2O$; 1.0 vc (3 l) of 0.5 N NaOH; 1.0 vc (3 l) of Buffer E and finally 1.5 vc (4.5 l) of Buffer D–Buffer E in a 93.5:6.5 ratio.

Once the column was equilibrated, the material to be chromatographed was loaded. Said loading was performed at room temperature at 39 cm/hour. Thereafter, the elution was performed at the same flow rate and temperature, and the solutions and buffers hereinafter detailed were passed through it in the following order: 1.5 vc (4.5 l) of Buffer D–Buffer E in a 93.5:6.5 ratio. Thereafter, a gradient of Buffer D–Buffer E was applied starting from a 93.5:6.5 ratio of said buffers until a 50:50 ratio of said buffers in a total volume of 2.0 vc (6 l) was reached. Once the gradient was finished, 1.5 vc (4.5 l) of Buffer E was passed through the column. The selected EPO containing fractions were filtered under sterile conditions through a 0.22 $\mu$m pore membrane and stored at 4° C.

Example 6

Concentration and Diafiltration

The fractions resulting from the previous example were concentrated and diafiltered according to the following parameters and conditions:

1. Equipment
   A. Peristaltic pump: Watson Marlow - Cat. N ° 302S
   B. Tubing: Masterflex - Cat. N ° 06402-18
   C. Concentrator: Prep Scale Millipore CDU F002LC
2. Solutions and buffers:
   A. 10 mM Sodium Dodecyl Sulfate (SDS)
   B. 1 mM Triton X-100
   C. 0.1 N NaOH
   D. $H_2O$
   E. Buffer B: 10 mM $NaH_2PO_4$, 0.15 M NaCl, 0.05 mg/ml Lactose, pH 7.2
3. Material to be processed:
   A. Selected fractions resulting from the previous step.
   B. Sample conditions:
      1. Volume: 6,000 ml
      2. Conductivity: 5,000–8,000 $\mu$Si/cm
      3. pH:6.0

The equipment was first, cleaned, sanitized and equilibrated, letting pass through it the following sequence of solutions and buffers: 10 l of 10 mM SDS; 40 l of $H_2O$; 10 l of 1 mM Triton X-100, 40 l of $H_2O$; 10 l of 0.1N NaOH; 40 l of $H_2O$ and finally 5 l of Buffer B. In this way, the equipment was ready to be used for the concentration and diafiltration procedures against Buffer B on the selected fractions, following the usual methodology.

The final volume of the concentrated product was 350–600 ml, its conductivity was 15,500–19,000 mSi/cm, the pH was 7.2, and the solution was stored at 4° C.

Example 7

Molecular Exclusion Chromatography

The material resulting from the previous example was chromatographed using a molecular exclusion matrix, as follows:

1. Equipment:
   A. Column:
      1) Diameter: 10 cm
      2) Bed height: 76 cm
      3) Matrix
         a) Sephacryl S-200 HP (Pharmacia)
         b) Volume: 6,000 ml
2. Solutions and buffers:
   A. Buffer B: 10 mM $NaH_2PO_4$, 0.15M NaCl, 0.05 mg/ml Lactose, pH 7.2
   B. 0.5N NaOH
3. Material to be chromatographed
   A. Fractions selected from the previous example, concentrated.
   B. Sample conditions:
      1. Volume: 350 to 600 ml
      2. Conductivity: 15,500–19,000 $\mu$Si/cm
      3. pH: 7.2

To equilibrate the column the following solutions or buffers in the quantities hereinafter detailed were sequentially passed through it: 1.0 volume of the column ("vc") (6 l) of $H_2O$; 1.5 vc (9 l) of 0.5 N NaOH and finally 3.0 vc (18 l) of Buffer B. Once the column was equilibrated, 100 ml from the material to be chromatographed were loaded. Said loading was performed at room temperature at 27 cm/hour. Thereafter, the elution was performed at the same flow and temperature rates, and 0.75 vc (4.5 l) of Buffer B was passed through it. This procedure was repeated between four to six times, that is, until the material to be chromatographed was completely utilized. The selected EPO containing fractions were filtered under sterile conditions through a 0.22 $\mu$m pore membrane and stored at 4° C.

With this step the purification process was concluded. The EPO obtained has a purity degree superior to 99% and the entire purification process had a global yield of approximately 30%.

Example 8

EPO Assays

The EPO obtained in the previous example was assayed for identity and biological activity according to the following protocol.

In a denaturing SDS-PAGE gel the EPO was identified as a wide band of molecular weight as expected for EPO. See FIG. 1. The band was recognized by monoclonal and polyclonal antibodies raised against human EPO in a Western blot assay as expected for EPO. See FIG. 2. The treatment with glycanases proved the existence of the glycosidic chains in the extent and size as expected for EPO. See FIG. 3. The EPO produced was shown to be composed of a series of species showing isoelectric points from 3.0 to 4.5 as expected for EPO. See FIG. 4.

The complete amino acid sequence of the isolated protein, purified from the culture supernatant of transfected cell lines showed total homology with natural human erythropoietin whose 165 aminoacid sequence is as follows (SEQ ID NO:1):

| NH$_2$— | Ala | Pro | Pro | Arg | Leu | Ile | Cys | Asp |
|---|---|---|---|---|---|---|---|---|
| | Ser | Arg | Val | Leu | Glu | Arg | Tyr | Leu |
| | Leu | Glu | Ala | Lys | Glu | Ala | Glu | |

The presence of the four glycosilation sites on the 165 amino acid chain, as well as the complex carbohydrate structure, and in particular, the sialic acid terminal residues, which characterize EPO were verified. These results were further supported by a biological activity assay of the produced protein by an ex-hypoxic polycythemic mice test, which showed complete concordance with the international EPO standard.

An EPO sample obtained according to the claimed method was submitted to a reverse phase and molecular exclusion high performance liquid chromatography analysis. In both cases, a purity over 99% was proved. See FIGS. 5 and 6.

The following table illustrates the recovery of each separation step corresponding to the claimed procedure.

| STAGE | RECOVERY (%) |
|---|---|
| Cell Culture Supernatant | 100 |
| Hydrophobic Interaction Chromatography | 70 |
| Concentration and Diafiltration I | 97 |
| Anionic Exchange Chromatography | 82 |
| Cationic Exchange Chromatography | 71 |
| Concentration and Diafiltration II | 95 |
| Molecular Exclusion Chromatography | 79 |

The following table illustrates the accumulated recovery of the purification sequence claimed in claim 2.

| STAGE | RECOVERY (%) |
|---|---|
| Cell Culture Supernatant | 100 |
| Hydrophobic Interaction Chromatography | 70 |
| Concentration and Diafiltration I | 68 |
| Anionic Exchange Chromatography | 56 |
| Cationic Exchange Chromatography | 40 |
| Concentration and Diafiltration II | 38 |
| Molecular Exclusion Chromatography | 30 |

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. A method of purifying recombinant human erythropoietin from cell culture supernatants comprising the following steps in order:
   (a) differential saline precipitation;
   (b) hydrophobic interaction chromatography;
   (c) concentration and diafiltration;
   (d) anionic exchange chromatography;
   (e) cationic exchange chromatography;
   (f) concentration and diafiltration; and
   (g) molecular exclusion chromatography.

2. The method of claim 1, wherein step (a) comprises adding ammonium sulfate to said culture supernatant, followed by centrifugation.

3. The method of claim 1, wherein step (b) comprises using a hydrophobic interaction matrix.

4. The method of claim 3, wherein said hydrophobic interaction matrix is Phenyl Sepharose 6 Fast Flow.

5. The method of claim 1, wherein step (d) comprises using an anionic exchange matrix.

6. The method of claim 5, wherein said anionic exchange matrix is Q-Sepharose Fast Flow.

7. The method of claim 1, wherein step (e) comprises using a cationic exchange matrix.

8. The method of claim 7, wherein said cationic exchange matrix is SP-Sepharose Fast Flow.

9. The method of claim 1, wherein step (g) comprises using a molecular exclusion matrix.

10. The method of claim 9, wherein said molecular exclusion matrix is Sephacryl S-200 HP.

11. A method of purifying recombinant human erythropoietin from cell culture supernatants comprising the following steps in order:
   (a) differential saline precipitation;
   (b) concentration and diafiltration;
   (c) anionic exchange chromatography;
   (d) cationic exchange chromatography;
   (e) hydrophobic interaction chromatography;
   (f) concentration and diafiltration; and
   (g) molecular exclusion chromatography.

12. The method of claim 11, wherein step (a) comprises adding ammonium sulfate to said culture supernatant, followed by centrifugation.

13. The method of claim 11, wherein step (c) comprises using an anionic exchange matrix.

14. The method of claim 13, wherein said anionic exchange matrix is Q-Sepharose Fast Flow.

15. The method of claim 1, wherein step (d) comprises using a cationic exchange matrix.

16. The method of claim 15, wherein said cationic exchange matrix is SP-Sepharose Fast Flow.

17. The method of claim 1, wherein step (e) comprises using a hydrophobic interaction matrix.

18. The method of claim 17, wherein said hydrophobic interaction matrix is Phenyl Sepharose 6 Fast Flow.

19. The method of claim 1, wherein step (g) comprises using a molecular exclusion matrix.

20. The method of claim 19, wherein said molecular exclusion matrix is Sephacryl S-200 HP.

* * * * *

UNITED STATES PATENT AND TRADEMARK OFFICE
CERTIFICATE OF CORRECTION

PATENT NO. : 7,012,130 B1 Page 1 of 1
APPLICATION NO. : 09/830964
DATED : March 14, 2006
INVENTOR(S) : Carcagno et al.

It is certified that error appears in the above-identified patent and that said Letters Patent is hereby corrected as shown below:

In column 12, line 21, delete "claimed in claim 2" and insert "claimed in claim 1".

Signed and Sealed this

Eleventh Day of July, 2006

JON W. DUDAS
*Director of the United States Patent and Trademark Office*

UNITED STATES PATENT AND TRADEMARK OFFICE
CERTIFICATE OF CORRECTION

PATENT NO. : 7,012,130 B1 Page 1 of 1
APPLICATION NO. : 09/830964
DATED : March 14, 2006
INVENTOR(S) : Carcagno et al.

It is certified that error appears in the above-identified patent and that said Letters Patent is hereby corrected as shown below:

In column 14, claim 15, Line 38, delete "method of claim 1" and insert --method of claim 11--.

In column 14, claim 17, Line 42, delete "method of claim 1" and insert --method of claim 11--.

In column 14, claim 19, Line 47, delete "method of claim 1" and insert --method of claim 11--.

Signed and Sealed this

Tenth Day of April, 2007

JON W. DUDAS
*Director of the United States Patent and Trademark Office*

SEQUENCE LISTING

<160> NUMBER OF SEQ ID NOS: 1

<210> SEQ ID NO 1
<211> LENGTH: 165
<212> TYPE: PRT
<213> ORGANISM: Homo sapiens

<400> SEQUENCE: 1

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80
```

-continued

```
Leu Val Asn Ser Ser Gln Pro Trp Glu Pro Leu Gln Leu His Val Asp
             85              90                  95

Lys Ala Val Ser Gly Leu Arg Ser Leu Thr Thr Leu Leu Arg Ala Leu
            100             105             110

Gly Ala Gln Lys Glu Ala Ile Ser Pro Pro Asp Ala Ala Ser Ala Ala
        115             120             125

Pro Leu Arg Thr Ile Thr Ala Asp Thr Phe Arg Lys Leu Phe Arg Val
    130             135             140

Tyr Ser Asn Phe Leu Arg Gly Lys Leu Lys Leu Tyr Thr Gly Glu Ala
145             150             155                         160

Cys Arg Thr Gly Asp
                165
```